United States Patent [19]
Grislain et al.

[11] Patent Number: 5,433,958
[45] Date of Patent: Jul. 18, 1995

[54] PHARMACEUTICAL DOSAGE UNIT FOR RECTAL ADMINISTRATION

[75] Inventors: Luc Grislain, Blanquefort; Elisabeth Le Huede; Olivier Louis, both of Bordeaux, all of France

[73] Assignee: Asta Medica Aktiengesellschaft, Dresden, Germany

[21] Appl. No.: 216,840

[22] Filed: Mar. 24, 1994

[30] Foreign Application Priority Data

Apr. 13, 1993 [FR] France .................. 93 04323

[51] Int. Cl.⁶ ............................................. A61K 9/48
[52] U.S. Cl. ........................... 424/436; 424/434; 424/456; 424/465; 424/489; 514/882; 514/966
[58] Field of Search ............ 424/486, 484, 436, 469, 424/471, 472, 474, 457, 992; 514/966, 965, 962

[56] References Cited

U.S. PATENT DOCUMENTS

| | | | |
|---|---|---|---|
| 3,577,512 | 5/1971 | Shepherd et al. | 424/457 |
| 3,851,051 | 11/1974 | Miskel et al. | 424/456 |
| 4,406,896 | 9/1983 | Higuchi et al. | 514/966 |
| 4,708,834 | 11/1987 | Cohen et al. | 424/456 |
| 4,894,239 | 1/1990 | Nonomura et al. | 424/469 |
| 4,938,967 | 7/1990 | Newton et al. | 424/469 |
| 5,182,270 | 1/1993 | Musson et al. | 514/58 |
| 5,271,946 | 12/1993 | Hettche | 514/826 |

FOREIGN PATENT DOCUMENTS 0041665 12/1981 European Pat. Off. .
0137364  4/1985 European Pat. Off. .
0147479  7/1985 European Pat. Off. .

Primary Examiner—Thurman K. Page
Assistant Examiner—Pamela S. Webber
Attorney, Agent, or Firm—Cushman, Darby & Cushman

[57] ABSTRACT

A pharmaceutical dosage unit defined by a sheath composed of a bioadhesive material which surrounds one or more capsules and one or more nonliquid supports containing the active pharmaceutical ingredient. The capsules are made of a mixture of approximately 70% gelatin and 30% glycerin. The supports can be tablets. The dosage unit is useful in providing a sustained release effect of the pharmaceutical ingredient in the lower part of the rectum for a period of 24 hours.

15 Claims, 1 Drawing Sheet

PHARMACEUTICAL DOSAGE UNIT FOR RECTAL ADMINISTRATION

The present invention relates to a new pharmaceutical dosage unit for rectal administration of pharmacologically active compounds.

BACKGROUND OF THE INVENTION

The rectal administration of pharmacologically active molecules is widely used. This form of administration has the advantage over oral administration in that it is unaffected by the ingestion of foods, nausea or low intestinal absorption. It can be used in patients who are incapable of salivating, who are unconscious or who have to go without food before an operation.

Nevertheless, since the rectum is made up of zones differing in their characteristics, the effects of treatment by rectal administration vary according to the pharmaceutical forms used and their anatomical positioning.

Thus, the positioning of a pharmaceutical dosage unit in the lower part of the rectum enables the active ingredient which it contains to pass directly into the general circulation. Dosage forms positioned in the upper or middle part of the rectum enable the active ingredients which they contain to pass into the portal system. In that case, the active ingredient is in danger of undergoing metabolic degradation in the liver.

Dosage units which provide for specific administration in the lower part of the rectum have already been described in the literature. They have outer surfaces comprising bioadhesive substances which facilitate their retention by the layer of mucus covering that part of the rectum. This retention prevents the pharmaceutical dosage unit from moving towards the upper parts of the rectum.

Suppositories containing fats are unsuitable for this application because they cannot be retained in the lower part of the rectum on account of their composition. Suppositories made of hydrogels, such as polyethylene glycol, which are impregnated with pharmacologically active substances have also been described (Cole et al., Br J. Clin. Pharmac. 1990, 30, 781–786).

Gelatin sheaths containing various active ingredients have also been tested for rectal administration.

These sheaths are positioned in the lower part of the rectum where they deliver the active ingredient which they contain (Brumley et al., The Hospice Journal, Vol. 4(1) 1988; Maloney et al., The American Journal of Hospice Care, July/August 1989, 6(4), 34–35).

These pharmaceutical dosage units allow the active ingredient to pass into the circulation without being metabolized by the liver.

Nevertheless, this type of pharmaceutical dosage unit is variously accepted by patients with dry rectal mucosa and does not meet all the requirements of treatments involving this method of administration.

SUMMARY OF THE INVENTION

The object of the present invention is to provide a pharmaceutical dosage unit which, even in the event of drying out of rectal mucosa, provides for improved absorption by the rectal mucosa of the active ingredient present in the pharmaceutical dosage unit.

According to the invention, it has surprisingly been found that pharmaceutical dosage units containing large quantities of hygroscopic substances, i.e. substances establishing a supply of water at the level of the rectal mucosa, enable better passage of the active ingredient into the circulation, while maintaining effective hydration of the mucosa.

It has also been found that the supply of water established by the presence of hygroscopic substances enables the pH of the mucosa to be reduced to optimal values for the passage of certain active ingredients.

Accordingly, the present invention relates to a pharmaceutical dosage for the rectal administration of at least one pharmacologically active compound which is assimilable in the lower part of the rectum, the said pharmaceutical dosage unit consisting of a sheath of which the outer wall comprises a material with bioadhesive properties, the interior of the sheath containing the combination of:

(a) at least one capsule containing at least one hygroscopic substance and
(b) an effective quantity of the said pharmacologically active compound in a non-liquid form.

In order to establish a supply of water, the said pharmaceutical dosage unit contains significant quantities of hygroscopic substances (a).

The ratio by weight of the quantities of hygroscopic substances contained in the sheath and capsules to the quantities of non-hygroscopic substances is advantageously at least 1.5:1 and preferably at least 2:1.

One such pharmaceutical dosage unit may thus contain a quantity of hygroscopic substances of at least 400 mg and preferably 600 mg per dosage unit.

The hygroscopic substances may be gelatin or glycerin, used individually or in the form of a mixture of them, or a mixture or one or both of them with any pharmaceutically acceptable hygroscopic substance.

The constituent material of the wall of the sheath is gelatin while the capsule(s) comprise a mixture of gelatin and glycerin.

The supply of water established by the proteins forming the membrane of the sheath and the hygroscopic capsules has the effect of reducing or maintaining the pH of the rectal mucosa which is favorable to the rectal administration of numerous active principles.

The absorption of compounds of this type and their passage into the circulation are thus increased.

The quantity of active ingredient present in the pharmaceutical dosage unit, according to the invention, varies according to the nature of the active ingredient and the desired posology. For example, for the active ingredient Carlytene or Moxisylyte, see Vidal, 1992, page 234), the quantity of active ingredient per dose may be between 30 and 500 mg and, for the active ingredient azelastine (see Merck Index, 11th Ed., page 926, No. 922), the quantity of active ingredient per dose may be between about 2 and 12 mg.

In an even more preferred embodiment, the pharmaceutical dosage unit consists of a sheath of gelatin, the sheath containing:

(a) one or more capsules consisting of a mixture of gelatin and glycerin,
(b) one or more vehicles or supports containing the active ingredient, the supports being non-liquid.

In one particular embodiment, the proportions by weight in the capsules are of the order of 70% of gelatin and 30% of glycerin.

One particularly simple embodiment of the support consists of one or more tablet(s) containing the active ingredient which are accommodated in the sheath. The following examples use tablets although the invention is by no means limited to such supports. It is also possible to use microgranules containing the active ingredient which are either free or accommodated in a sheath or capsule of their own. The expression "tablets" also encompasses pellets, pills and other solid galenic forms typically used for the administration of pharmaceutically active ingredients. The pharmaceutically active ingredients in particular may also be contained in gels.

The arrangement of the supports and capsules in the sheath may vary according to the desired characteristics of the pharmaceutical unit. Illustrative examples are provided in the following with reference to FIGS. 1, 2 and 3 of the accompanying drawings.

The total quantity of hygroscopic substances present in the pharmaceutical unit according to the invention should be such that it is capable of establishing a supply of water providing for sufficient hydration of the rectal mucosa, although it should not be excessive in order to avoid a laxative effect.

In the context of the invention, a bioadhesive material is any substance which enables the pharmaceutical forms to adhere to the rectal mucosa. In the case of gelatin, the required adhesiveness may be established by contact and interpenetration of the gelatin chains with the mucus and then by coupling of the gelatin and mucus.

The principal advantages of the pharmaceutical dosage units according to the invention are as follows:
because they are administered by the rectal route, they do not undergo any modification during digestion and cannot be rejected by the patients, for example in the event of vomiting:
they may readily be administered to patients who cannot be treated by oral administration, particularly in cases of cancer of the upper aerodigestive tracts;
in the event of overdosage, the pharmaceutical forms may readily be eliminated by washing;
the pharmacologically active molecules are not metabolized by the liver by virtue of their passage through the portal system.

In addition, the pharmaceutical dosage units according to the invention have specific advantages, namely:
they have a better delayed-release effect than other rectal forms which enables them to be administered to patients every 24 hours and not every 12 hours or even less as is the case with the other rectal forms;
they show better reproducibility in regard to absorption of the active ingredient, both in various patients and in the event of repeated treatments for one and the same patient;
by virtue of the buffering capacity of the proteins constituting the gelatin of the sheaths, they enable the pH to be maintained in an optimal absorption range of the pharmacologically active compound with which it is desired to treat the patient.

The present invention lends itself to the formulation of numerous types of pharmaceutically active ingredients suitable for rectal administration. Non-limiting examples are provided hereinafter. The preferred category of active compounds is that of so-called matrix compounds in which the active ingredient is trapped in a polymer network from which it escapes slowly. A person skilled in the art of administering pharmaceuticals is thus in a position to determine the active ingredients which are suitable for carrying out the invention.

Supports, particularly tablets, having a delayed-release effect are generally preferred. Thus, the sustained-release dihydrocodeine tablets marketed in France under the name of "Dicoda" may be used in the pharmaceutical unit according to the invention.

The invention is illustrated by the following nonlimiting examples, in conjunction with the accompanying drawings, wherein:

Figure 1:
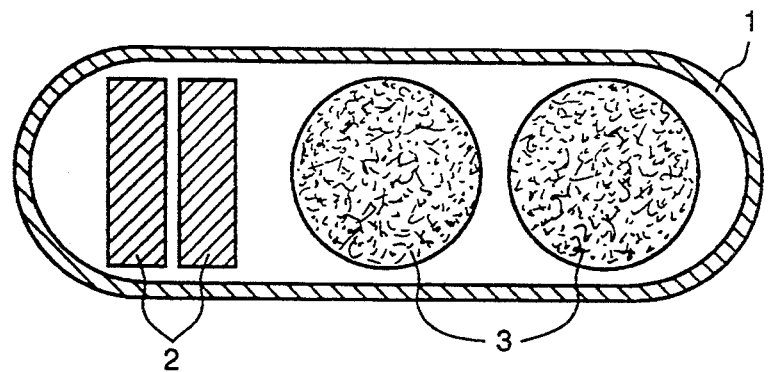
FIG. 1 schematically illustrates a pharmaceutical dosage unit which is composed of a sheath (1) which defines a cavity containing two tablets (2) and two capsules (3)

In the pharmaceutical dosage unit shown in FIG. 1, the sheath (1) surrounds two tablets (2) of pharmaceutically active compound and two hygroscopic capsules (3), the tablets (2) and the capsules (3) each occupying part of the sheath.

Figure 2:
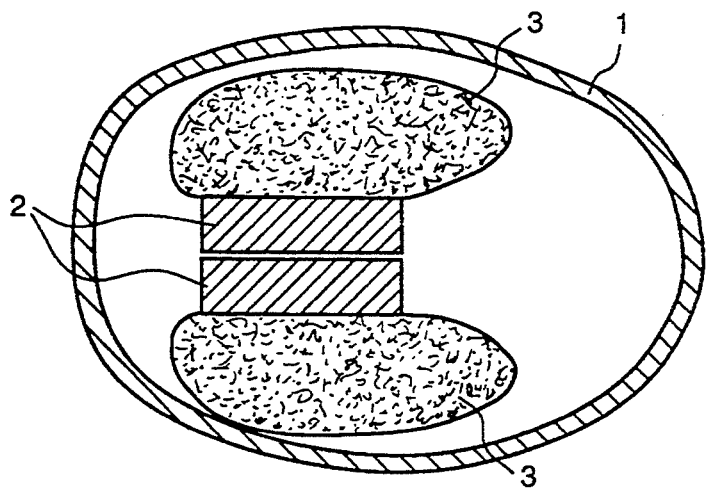
FIG. 2 schematically illustrates a pharmaceutical dosage unit which is composed of a sheath (1) which defines a cavity containing two tablets (2) sandwiched between two capsules (3)

FIG. 2 shows a pharmaceutical dosage unit in which the sheath (1) surrounds two tablets (2) sandwiched between two capsules (3). In this case, the introduction of the sheath into the rectum—in addition to dissolution of the sheath—allows the formation of an amalgam between the capsules and the tablets by softening of the capsules.

This amalgam delays the release of the pharmaceutically active compound and thus further improves the sustained release effect of the pharmaceutical dosage unit according to the invention.

Figure 3:
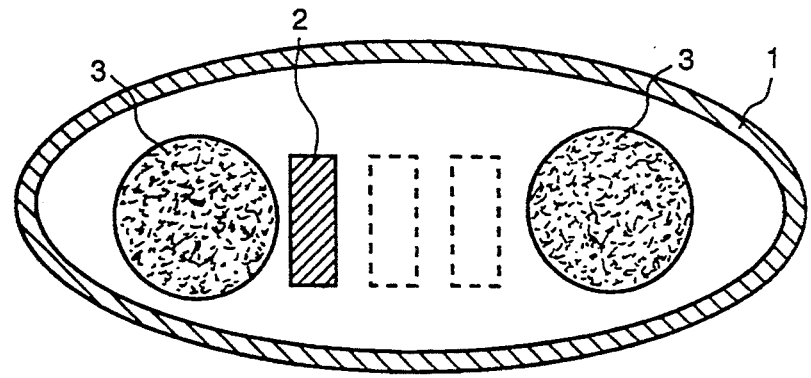
FIG. 3 schematically illustrates a further embodiment of the pharmaceutical dosage unit of FIG. 2 wherein the sheath (1) defines a cavity containing one to three tablets which are contained in a second sheath (not shown) which sheath containing tablets is sandwiched between two capsules (3).

FIG. 3 shows a pharmaceutical dosage unit in which the sheath (1) surrounds two capsules (3) arranged at either end of the sheath and one to three tablets (2) of active ingredient between the capsules.

The following examples are intended to illustrate the invention without limiting it in any way.

Tests were carried out with size 00 rectal sheaths containing two gelatin capsules each weighing 266 mg. Two active ingredients were tested, namely Carlytene in the form of 30 mg tablets and azelastine in the form of 4.4 mg tablets.

Two arrangements in the sheath were studied, namely:
the tablets are surrounded by the soft capsules in the following arrangement: capsule-tablet-capsule (c-cp-c for short), cf. FIG. 3;
the tablets are only in contact with a single soft capsule in the following arrangement: capsule-capsule-tablet (c-c-cp for short), cf. FIG. 1.

The tests comprised measuring the percentage of active ingredient (AP) released by dissolution as a function of time (in minutes). The procedure adopted for dissolution is described in Pharmacopée Européenne, 2nd Edition, Part 1, V.5.4.

The working conditions were as follows:
1) CARLYTENE 30 mg temperature: 37° C. medium: 500 ml water 1 tablet per reactor rotational speed of the blades 50 r.p.m. DO reading at 274 nm every 5 minutes 2) AZELASTINE 4.4 mg temperature: 37° C. medium: 500 ml 0.01N HCl 2 tablets per reactor rotational speed of the blades 100 r.p.m. DO reading at 285 nm every 5 minutes The results obtained are set out in Tables I and II below.

TABLE I

Carlytene 30 mg

% AP released

| Analysis time mins. | Arrangement No. 1 c-cp-c | Arrangement No. 2 -c-c-cp |
|---|---|---|
| 0 | 0.0 | 0.0 |
| 5 | 1.0 | 4.5 |
| 10 | 1.1 | 32.5 |
| 15 | 25.2 | 62.3 |
| 20 | 62.2 | 86.0 |
| 25 | 86.5 | 96.7 |
| 30 | 98.7 | 102.0 |
| 40 | 102.5 | 102.5 |

N.B.: With the single tablet, the AP release rate was 80% in 5 to 7 minutes.

TABLE II

Azelastine 4.4 mg

% AP released

| Analysis time mins. | Arrangement No. 1 c-cp-c | Arrangement No. 2 -c-c-cp |
|---|---|---|
| 0 | 0.0 | 0.0 |
| 5 | 7.3 | 20.2 |
| 10 | 39.8 | 70.7 |
| 15 | 60.5 | 87.3 |
| 20 | 74.7 | 94.7 |
| 25 | 82.8 | 96.9 |
| 30 | 88.9 | 99.3 |
| 40 | 95.0 | 98.2 |

N.B.: With the single tablet, the AP release rate was 80% in less than 15 minutes.

The rectal administration of pharmaceutical forms according to the invention thus provides for a greater delayed-release effect and for smaller variations in the concentration of active agent in the plasma.

Thus, the pharmaceutical dosage unit according to the invention enables active compounds to be administered to patients at longer intervals of the order of 24 hours for the same average activity. This advantage is reflected in improved comfort both for the patient and for the nursing personnel.

What is claimed is:

1. A pharmaceutical dosage unit for the rectal administration of at least one pharmaceutically active compound which is assimilable in the lower part of the rectum comprising a sheath, capsule(s) and support(s) containing at least one pharmaceutically active compound wherein the sheath which is composed of a bioadhesive material surrounds a cavity structure which contains within it said capsule(s) which contains at least one hygroscopic substance and said support(s) which contains a pharmaceutically effective amount of said pharmaceutically active compound in a non-liquid form which support is selected from the group consisting of tablets, microgranules and gels.

2. A pharmaceutical dosage unit as claimed in claim 1 in which the ratio by weight of the quantity of hygroscopic substance contained in the sheath and the capsules to the quantity of non-hygroscopic substances is at least 1.5:1.

3. A pharmaceutical dosage form as set forth in claim 2 in which the ratio by weight of the quantity of hygroscopic substance contained in the sheath and the capsules to the quantity of non-hygroscopic substances is at least 2:1.

4. A pharmaceutical dosage unit as claimed in claim 1 or claim 2 in which the quantity of hygroscopic substances is at least 400 mg per dosage unit.

5. A pharmaceutical dosage unit as claimed in claim 4 in which the quantity of hygroscopic substances is at least 600 mg.

6. A pharmaceutical dosage unit as set forth in claim 1 in which the microgranules are free.

7. A pharmaceutical dosage unit as set forth in claim 1 in which the microgranules are contained within a second sheath.

8. A pharmaceutical dosage unit as claimed in claim 1 or claim 2 in which the pharmacologically active compound is in the form of a matrix compound in which the active compound is trapped in a polymer network from it escapes slowly.

9. A pharmaceutical dosage unit as claimed in any of claims 1 to 2 in which the bioadhesive material is gelatin.

10. A pharmaceutical dosage unit as defined in claim 1 or claim 2 in which the capsule is made of a material selected from the group consisting of gelatin, glycerin and mixture thereof.

11. A pharmaceutical dosage unit as claimed in claim 1 or claim 2 wherein there are multiple supports and multiple capsules which are juxtaposed respectively as groups in close proximity.

12. A pharmaceutical dosage unit as claimed in claim 1 or claim 2 wherein 1) the sheath is composed of gelatin, 2) at least one capsule is composed of a mixture of gelatin and glycerin and 3) there are one or more supports which are non-liquid.

13. A pharmaceutical dosage unit as set forth in claim 12 in which the capsule is made of a quantity by weight of approximately 70% of gelatin and 30% of glycerin.

14. A pharmaceutical dosage unit as set forth in claim 12 in which the supports are tablets.

15. A pharmaceutical dosage unit as claimed in claim 12 in which the supports are sandwiched between two capsules.

* * * * *